US008172893B2

(12) United States Patent
Moore

(10) Patent No.: US 8,172,893 B2
(45) Date of Patent: May 8, 2012

(54) EXPANDABLE STENT

(75) Inventor: Brian E. Moore, Sunnyvale, CA (US)

(73) Assignee: Medtronic, Inc., Minneapolis, MN (US)

( * ) Notice: Subject to any disclaimer, the term of this patent is extended or adjusted under 35 U.S.C. 154(b) by 215 days.

(21) Appl. No.: 11/745,877

(22) Filed: May 8, 2007

(65) Prior Publication Data

US 2008/0119926 A1    May 22, 2008

Related U.S. Application Data

(63) Continuation of application No. 10/778,606, filed on Feb. 17, 2004, now abandoned, which is a continuation of application No. 09/946,137, filed on Sep. 5, 2001, now Pat. No. 6,746,477, which is a continuation of application No. 09/522,292, filed on Mar. 9, 2000, now abandoned.

(51) Int. Cl.
*A61F 2/90* (2006.01)

(52) U.S. Cl. ........................................ 623/1.15; 623/1.17

(58) Field of Classification Search .................. 623/1.17, 623/23.7–23.71
See application file for complete search history.

(56) References Cited

U.S. PATENT DOCUMENTS

| 5,695,516 A | 12/1997 | Fischell et al. |
| 5,697,971 A | 12/1997 | Fischell et al. |
| 5,843,175 A | 12/1998 | Frantzen |
| 5,895,406 A | 4/1999 | Gray et al. |
| 5,931,866 A | 8/1999 | Frantzen |
| 6,231,599 B1 | 5/2001 | Ley |
| 6,540,775 B1 | 4/2003 | Fischell et al. |

FOREIGN PATENT DOCUMENTS

| WO | 97/26840 | | 1/1997 |
| WO | WO/98/35634 | * | 8/1998 |

* cited by examiner

*Primary Examiner* — Thomas J Sweet
*Assistant Examiner* — Suba Ganesan

(57) ABSTRACT

A stent has a porous surface having a repeating pattern generally in the shape of a "butterfly" comprising alternative concave and convex segments which give the stent good flexibility when unexpanded, and good shape retention once expanded.

11 Claims, 1 Drawing Sheet

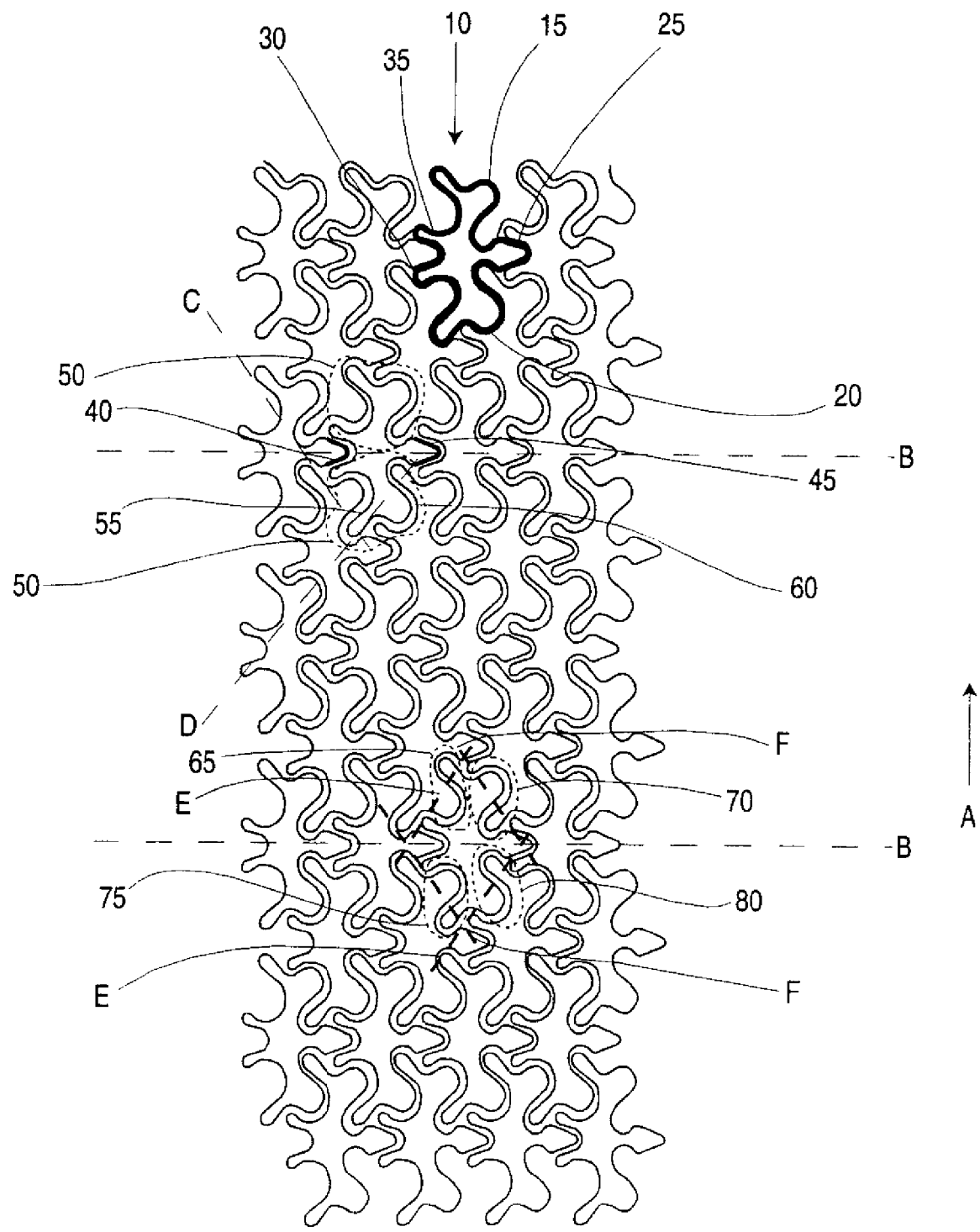

EXPANDABLE STENT

This application is a continuation of copending application Ser. No. 10/778,606, which was a continuation of Ser. No. 09/946,137 (now U.S. Pat. No. 6,746,477), which was a continuation of Ser. No. 09/522,292, now abandoned.

BACKGROUND OF THE INVENTION

1. Field of the Invention

The present invention relates to an expandable stent.

2. Brief Description of the Prior Art

The term "stent" has been used interchangeably with terms such as "intraluminal vascular graft" and "expansible prosthesis". Throughout this specification the term "stent" is intended to mean any expandable prosthetic device for implantation in a body passageway (e.g., a lumen or artery).

The use of stents has attracted an increasing amount of attention due the potential of these devices to be used, in certain cases, as an alternative to surgery. Generally, a stent is used to obtain and maintain the patency of the body passageway while maintaining the integrity of the passageway. As used in this specification, the term "body passageway" is intended to mean any duct (e.g., natural or iatrogenic) within the human body, including blood vessels, respiratory ducts, gastrointestinal ducts and the like.

Stent development has evolved to the point where the vast majority of currently available stents rely on controlled plastic deformation of the entire structure of the stent at the target body passageway so that only sufficient force to maintain the patency of the body passageway is applied during expansion of the stent.

Generally, in many of these systems, a stent, in association with a balloon, is delivered to the target area of the body passageway by a catheter system. Once the stent has been properly located (for example, for intravascular implantation the target area of the vessel can be filled with a contrast medium to facilitate visualization during fluoroscopy), the balloon is expanded thereby plastically deforming the entire structure of the stent so that the latter is urged in place against the body passageway. The amount of force applied is at least that necessary to expand the stent (i.e., the applied force exceeds the minimum force above which the stent material will undergo plastic deformation) while maintaining the patency of the body passageway. At this point, the balloon is deflated and withdrawn within the catheter, and is subsequently removed. Ideally, the stent will remain in place and maintain the target area of the body passageway substantially free of blockage (or narrowing).

In the design of any new stent there are generally two functional constraints which govern the usefulness of the stent. First, the stent should have a high degree of flexibility in the unexpanded state. This is needed to facilitate navigation of the stent through tortuous anatomy to the location of the target stenosis. Second, the expanded stent should be radially rigid to minimize the effects of restenosis and the possibility of acute occlusion. Thus, an ideal stent would be characterized by divergent functional properties depending on the state of the stent (i.e., expanded or unexpanded).

Conventionally, the stent properties of flexibility in the unexpanded state and radial rigidity in the expanded state have been achieved using one set of interconnected struts (typically the longitudinal struts) to confer flexibility to the unexpanded stent and another pair of interconnected struts (typically non-longitudinal circumferential rings of struts) which open up to radially rigid hoop structures (in the ideal case) to confer radial rigidity to the expanded stent.

Unfortunately, this approach complicates the design exercise. Further, depending on whether the stent is in the expanded or unexpanded state, only a portion of the struts are being used (i.e., to confer flexibility or radial rigidity).

Accordingly, it would be desirable to have an improved stent which overcomes these disadvantages. It would be further desirable if the improved stent could be manufactured readily. It would be further desirable if the improved stent could be deployed using conventional stent delivery systems.

SUMMARY OF THE INVENTION

It is an object of the present invention to provide a novel expandable stent which obviates or mitigates at least one of the above-mentioned disadvantages of the prior art.

Accordingly, in one of its aspects, the present invention provides an unexpanded stent comprising a proximal end and a distal end in communication with one another, a tubular wall disposed between the proximal end and the distal end, the tubular wall having a longitudinal axis and a porous surface defined by a plurality of interconnected circumferential rows of a repeating pattern, the repeating pattern comprising a concave-shaped wall and a convex-shaped wall aligned substantially along an axis substantially orthogonal to the longitudinal axis.

In another of its aspects, the present invention provides an unexpanded stent comprising a proximal end and a distal end in communication with one another, a tubular wall disposed between the proximal end and the distal end, the tubular wall having a longitudinal axis and a porous surface defined by a plurality of interconnected circumferential rows of a repeating pattern, the repeating pattern comprising a concave-shaped wall and a convex-shaped wall aligned in manner such that individual repeating patterns in the a circumferential row are interlocked with respect to one another.

In another of its aspects, the present invention provides an unexpanded stent comprising a proximal end and a distal end in communication with one another, a tubular wall disposed between the proximal end and the distal end, the tubular wall having a longitudinal axis and a porous surface defined by a plurality of interconnected circumferential rows of a repeating pattern, the repeating pattern comprising four S-shaped sections orientated such that, for at least two pairs of the S-sections, one S-shaped section is a mirror image of the other S-shaped section along an axis orthogonal to the longitudinal axis.

In yet another of its aspects, the present invention provides an expandable stent comprising a proximal end and a distal end in communication with one another, a tubular wall disposed between the proximal end and the distal end, the tubular wall having a longitudinal axis and a porous surface defined by a plurality of interconnected circumferential rows of a repeating pattern, the repeating pattern being substantially free of straight sections and having a multi-lobed shaped perimeter and being oriented in place by at least six 3-point junctions.

BRIEF DESCRIPTION OF THE DRAWINGS

Embodiments of the present invention will be described with reference to the accompanying drawing which illustrates a two-dimensional view of a preferred design of the present stent.

DETAILED DESCRIPTION OF THE PREFERRED EMBODIMENTS

Thus, the present inventors have developed a novel stent design which has flexibility characteristics superior to currently available stent structures. Further, once the present stent is expanded, it exhibits an inherent tendency to maintain the longitudinal shape of the lumen in which it is deployed. This is a significant advantage of the present stent compared to many currently available stents. Specifically, upon expansion, many currently available stents tend to stretch and deform the lumen along its length from its natural orientation as the stent tends to straighten.

The present stent is characterized by a repeating pattern containing a strut architecture in which a given strut in the repeating pattern serves the dual role of flexibility and expansion/radial rigidity in the two states of the stent. Thus, the present stent is particularly robust in situations of complex deformation states that may be encountered in vivo. This includes (but is not limited to) simultaneous bending, calcific lesions, torsion and expansion. The present stent also has desirable uniformity of expansion under extreme conditions.

The present stent deforms with minimal or no distortion and with minimal or no significant deformations in localized areas. The deformation is smooth and thus the cylindrical profile is smooth.

Upon expansion, the repeating pattern in the present stent becomes expanded, ideally to a truss-like shape, which results in very desirable radial rigidity. Further, the present stent has a desirable strut density when expanded thereby resulting in excellent vessel coverage while allowing side branch access.

Other advantages of the present stent design will be readily apparent to those of skill in the art.

The present stent may be constructed from any suitable starting material. Preferably, the starting material is a thin tube of a metal or alloy. Alternatively, it is possible to construct the present stent from a flat sheet which preferably is cut (as described below), rolled and then welded.

In one preferred embodiment, the starting material may be one which is plastically deformable. Non-limiting examples of such a material include stainless steel, titanium, tantalum and the like. In another preferred embodiment, the starting material may be one which expands via temperature-dependent memory (i.e., a material which will expand upon reaching a certain temperature)—non-limiting examples of such a material include nitinol and the like.

With reference to the accompanying FIGURE, there is illustrated a two-dimensional view of a preferred design of the present stent. Thus, the illustrated view is derived by unrolling a side elevation of tubular stent.

The illustrated design may be produced by any of a number of known techniques. For example, it is preferred to produce the present stent by starting with a solid tube material (i.e., cylindrical with no porous surface) and then subjected the tube material to processing which results in removal of a portion thereof to define a porous surface. While the precise nature of this processing is not particularly restricted, it is preferred that the processing be effected on a computer programmable, laser cutting system which operates by:

(i) receiving the solid tube;

(ii) moving the solid tube longitudinally and rotationally under a laser beam to selectively remove sections of the solid tube thereby defining a porous surface; and (iii) cutting stent sections of desirable length of the solid tube.

A suitable such laser cutting system is known in the art as the LPLS-100 Series Stent Cutting Machine. The operation of this system to produce the unexpanded stent is within the purview of a person skilled in the art.

Thus, the stent produced from the laser cutting system is in the unexpanded state. i.e., the stent will exhibit elastic behavior in this state.

If desired, the stent may be subjected to further processing to apply a coating material thereon. The coating material may be disposed continuously or discontinuously on the surface of the stent. Further, the coating may be disposed on the interior and/or the exterior surface(s) of the stent. The coating material may be one or more of a biologically inert material (e.g., to reduce the thrombogenicity of the stent), a medicinal composition which leaches into the wall of the body passageway after implantation (e.g., to provide anticoagulant action, to deliver a pharmaceutical to the body passageway and the like) and the like.

The stent is preferably provided with a biocompatible coating, in order to minimize adverse interaction with the walls of the body vessel and/or with the liquid, usually blood, flowing through the vessel. The coating is preferably a polymeric material, which is generally provided by applying to the stent a solution or dispersion of preformed polymer in a solvent and removing the solvent. Non-polymeric coating material may alternatively be used. Suitable coating materials, for instance polymers, may be polytetraflouroethylene or silicone rubbers, or polyurethanes which are known to be biocompatible. Preferably, however, the polymer has zwitterionic pendant groups, generally ammonium phosphate ester groups, for instance phosphoryl choline groups or analogues thereof. Examples of suitable polymers are described in International patent publications WO-A-93/16479 and WO-A-93/15775. Polymers described in those specifications are haemocompatible as well as generally biocompatible and, in addition, are lubricious. When a biocompatible coating is used, it is important to ensure that the surfaces of the stent are completely coated in order to minimize unfavorable interactions, for instance with blood, which might lead to thrombosis.

This good coating can be achieved by suitable selection of coating conditions, such as coating solution viscosity, coating technique and/or solvent removal step. The coating, if present, can be applied to the stent in the expanded or contracted state. Preferably, the stent is applied to the coating in the contracted state.

With further reference to the accompanying FIGURE, the underlying stent structure has a longitudinal axis shown at arrow A.

As will be apparent to those of skill in the art, the illustrated embodiment has a repeating pattern generally in the shape of a "butterfly" 10. Butterfly 10 comprises a pair of wings 15, 20, an abdomen 25 and a pair of antennae 30, 35. Thus, as will be apparent to those of skill in the art, in the illustrated embodiment, butterfly 10 is an interlocking repeating pattern throughout the stent design.

The stent design may be envisaged as comprising a repeating pattern having a concave-shaped wall 40 and a convex-shaped wall 50 having apices aligned substantially along an axis B substantially orthogonal to longitudinal axis A. The repeating pattern is substantially free straight sections.

Preferably, concave-shaped wall 40 and the convex-shaped wall 45 are inter-connected by a pair of identical S-shaped walls 50 which are a mirror image about axis B. As illustrated, each S-wall 50 comprises one S-shaped section 55 having an axis C passing through an initial point and an end point of S-shaped section 55. Further, each S-wall 50 comprises one S-shaped section 60 having an axis D passing through an initial point and an end point of S-shaped section 60.

Preferably, the S-shaped section comprises an asymmetric pair of curved sections. As shown, each curved section comprises an arc of at least about 180°.

As shown, axis C and axis D are angled with respect to longitudinal axis A. Further, axis C and axis D are acutely angled with respect to one another.

Alternatively, the present stent may be envisaged as comprising a repeating pattern having four S-shaped sections 65, 70, 75, 80 oriented such that, for least two pairs of the S-sections, one S-shaped section is a mirror image of the other S-shaped section other along an axis orthogonal to the longitudinal axis—i.e., axis B. Thus, S-shaped section pair 65, 75 are mirror images of one another about axis B and S-shaped section pair 70, 80 are mirror images of one another about axis B.

As shown, it is preferred that the four S-shaped sections have substantially the same shape.

Further, the pair of S-shaped section 65, 80 each comprise an axis E passing through an initial point and an end point of the S-shaped section to define a pair of axes E in substantially parallel alignment. Still further, the pair of S-shaped sections 70, 75, each comprise axis F passing through an initial point and an end point of the S-shaped section to define a pair of axes F in substantially parallel alignment. As shown, axes E and F are angled with respect to longitudinal axis A. Furthermore, axes E and F are acutely angled with respect to one another.

The present stent may be used in a conventional manner. For example, the present stent may be mounted on a balloon expandable catheter and employed conventionally in a catheterization technique—see, for example, any of the references described above.

While the present invention has been described with reference to preferred and specifically illustrated embodiments, it will of course be understood by those skilled in the art that various modifications to these preferred embodiments and illustrated embodiments may be made without departing from the spirit and scope of the invention. For example, while the foregoing description has been in relation to the manufacture and use of a monotubular stent, those of skill in the art will immediately recognize that it is possible to employ the present stent in the form of a bifurcated stent. When the present stent is constructed as a bifurcated stent, it may be implanted using the procedure outlined in Canadian patent application 2,134,997. Such a bifurcated stent may be manufactured, inter alia, by any of the methods disclosed in the Canadian patent application number 2,175,720 filed on May 3, 1996. Other modifications which do not depart from the spirit and scope of the present invention will be apparent to those of skill in the art.

What is claimed is:

1. An unexpanded stent comprising
   A) a tubular element having a longitudinal axis and
   B) a porous surface comprising an array of apertures in a repeating pattern,
   C) wherein the repeating pattern has mirror-image symmetry about a transverse axis orthogonal to the longitudinal axis,
   D) each of the apertures of the unexpanded stent extends predominantly in a longitudinal direction,
   E) each of the apertures is defined by a boundary which, at least one point of tangency, is tangent to a line which is
      (a) perpendicular to said longitudinal axis and
      (b) intersects said boundary at least two points other than the point of tangency,
   F) said boundary has six junctions with neighboring boundaries, three on one side of said transverse axis and three on the opposite side thereof,
   G) the aperture boundary has a concave-shaped portion and a convex-shaped portion which are aligned so that repeating patterns in a circumferential row of apertures are interlocked with respect to one another,
   H) the concave-shaped portion and the convex-shaped portion being interconnected by a pair of lateral walls, one on either side of said transverse axis,
   I) each of said lateral walls comprising a pair of S-shaped sections lying on one respective side of said transverse axis, and
   J) each of said S-shaped sections comprising an asymmetric pair of curved sections,
   K) wherein each of said curved sections comprises an arc of at least 180°.

2. The unexpanded stent of claim 1, wherein each of the apertures in said pattern has at least ten changes from convex to concave concavity along its boundary.

3. The unexpanded stent of claim 1, wherein the repeating pattern is aligned substantially orthogonal to the longitudinal axis.

4. The stent defined in claim 1, wherein each lateral wall comprises:
   a first S-shaped section having a first axis passing through an initial point and an end point of the first S-shaped section and
   a second S-shaped section having a second axis passing through an initial point and an end point of the second S-shaped section.

5. The stent defined in claim 4, wherein each of the first axis and the second axis are angled with respect to the longitudinal axis.

6. The stent defined in claim 4, wherein the first axis and the second axis are acutely angled with respect to one another.

7. The unexpanded stent defined in claim 1, wherein each pair of the S-shaped sections is a mirror image of the other pair of S-shaped sections about said transverse axis.

8. The stent defined in claim 7, wherein all said S-shaped sections have substantially the same shape.

9. The stent defined in claim 7, wherein each of a first pair of S-shaped sections comprises a first axis passing through an initial point and an end point of the S-shaped section to define a pair of first axes in substantially parallel alignment.

10. The stent defined in claim 7, wherein each of a second pair of S-shaped sections comprises a second axis passing through an initial point and an end point of the S-shaped section to define a pair of second axes in substantially parallel alignment.

11. The stent defined in claim 7, wherein each of a first pair of S-shaped sections comprises a first axis passing through an initial point and an end point of the S-shaped section to define a pair of first axes in substantially parallel alignment; and each of a second pair of S-shaped sections comprises a second axis passing through an initial point and an end point of the S-shaped section to define a pair of second axes in substantially parallel alignment.

* * * * *